United States Patent

Degnan et al.

Patent Number: 4,465,884
Date of Patent: Aug. 14, 1984

[54] OLEFIN PROCESSING

[75] Inventors: Thomas F. Degnan, Yardley, Pa.; Leonard R. Koenig, Trenton, N.J.

[73] Assignee: Mobil Oil Corporation, New York, N.Y.

[21] Appl. No.: 408,954

[22] Filed: Aug. 17, 1982

[51] Int. Cl.³ .................................................. C07C 12/02
[52] U.S. Cl. .................................. 585/415; 585/407; 585/431
[58] Field of Search .............. 585/415, 533, 411, 431, 585/400, 407

[56] References Cited

U.S. PATENT DOCUMENTS

| | | |
|---|---|---|
| 3,803,256 | 4/1974 | Kirsch et al. ............... 260/673.5 |
| 4,021,331 | 5/1977 | Ciric ................................... 208/111 |
| 4,021,502 | 5/1977 | Plank et al. ..................... 585/533 |
| 4,347,395 | 8/1982 | Chu et al. |

Primary Examiner—Delbert E. Gantz
Assistant Examiner—Anthony McFarlane
Attorney, Agent, or Firm—Alexander J. McKillop; Michael G. Gilman; Dennis P. Santini

[57] ABSTRACT

The present invention relates to a process for conversion of feedstock comprising $C_3+$ olefins in the absence of added hydrogen over a catalyst comprising a crystalline zeolite having large pores and a high silica/alumina mole ratio.

10 Claims, 1 Drawing Figure

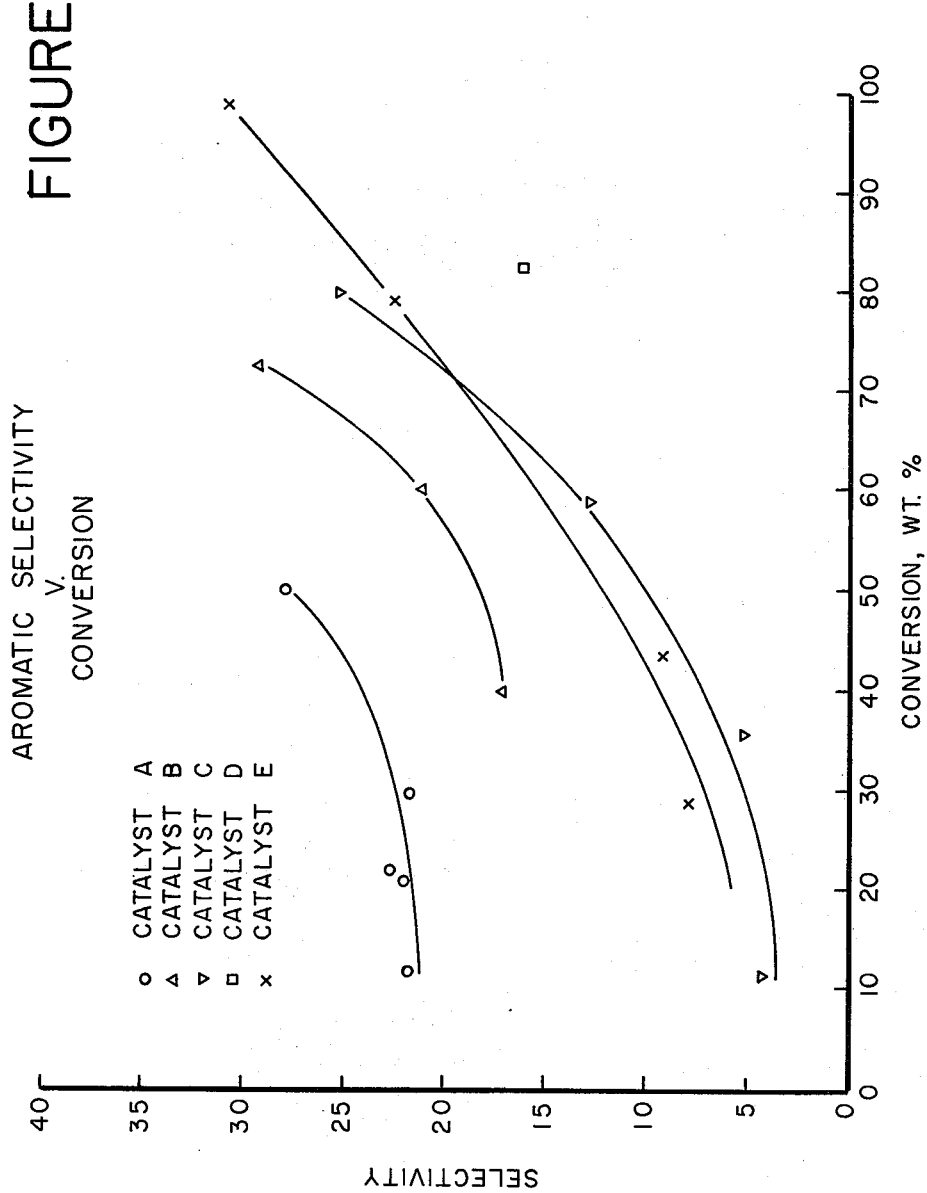

OLEFIN PROCESSING

BACKGROUND OF THE INVENTION

1. Field of the Invention

This invention relates to a process for conversion of feedstock comprising $C_3^+$ olefins in the absence of added hydrogen to product comprising non-aromatic hydrocarbons of higher molecular weight than the feedstock olefins and aromatics over a catalyst comprising a crystalline zeolite having large pores and a high silica/alumina mole ratio. The present process results in substantially reduced production of polynuclear aromatics and coke when compared to other olefin conversion processes.

2. Description of Prior Art

It has long been known to contact various hydrocarbon fractions with acidic catalysts generally and, in particular, with solid siliceous acidic catalysts, including those referred to as crystalline aluminosilicate zeolites. Contact of said hydrocarbon feed with said acid catalysts was carried out for a wide variety of reactions including cracking, isomerization, hydrocracking, etc. Representative U.S. patents disclosing and claiming contacting of various hydrocarbon fractions with crystalline aluminosilicates are U.S. Pat. Nos. 3,140,249; 3,140,251; 3,140,253 and 3,140,322.

The contact of paraffinic feedstocks with crystalline aluminosilicate zeolites is also known in the art. The primary reason for contacting paraffinic materials with zeolites has been for the purpose of cracking them, i.e. converting them to lower molecular weight products. Typical applications in this general field would be the use of crystalline aluminosilicate zeolites for carrying out dewaxing reactions, i.e. the cracking of paraffins to low molecular weight materials. U.S. Pat. No. 3,400,072, discloses a dewaxing process with crystalline aluminosilicates generally and U.S. Pat. No. 3,700,585, discloses and claims dewaxing operations carried out with a novel type of crystalline aluminosilicates identified as those of the ZSM-5 type.

U.S. Pat. No. 3,960,978 describes a process for making olefinic gasoline blending stock from $C_2$–$C_5$ olefin mixtures utilizing ZSM-5 type crystalline aluminosilicates. Other U.S. patents relating to converting various paraffins and/or olefins over ZSM-5 type zeolites include U.S. Pat. Nos. 3,760,024; 3,827,968; 4,100,218; 4,120,910 and 4,157,293. U.S. Pat. No. 3,760,024 claims a process for producing aromatic compounds from $C_2$–$C_4$ paraffins, olefins or mixtures thereof. U.S. Pat. No. 3,827,968 claims a process for conversion of $C_5^-$ olefin-containing gas to product comprising aromatics. U.S. Pat. No. 4,100,218 claims conversion of ethane through a series of process steps to a $C_5^+$ product useful as gasoline, LPG product and light fuel gas. U.S. Pat. No. 4,120,910 claims a process for converting a gaseous paraffinic hydrocarbon feedstock containing ethane to aromatic compounds. U.S. Pat. No. 4,157,293 claims a process for converting $C_2$–$C_{10}$ hydrocarbons consisting essentially of paraffins, olefins or their mixtures over a catalyst comprising a zeolite having a $SiO_2/Al_2O_3$ mole ratio of at least 12, a Constraint Index of 1 to 12 and containing zinc and another named metal.

The instant invention is not concerned with hydrocarbon compound conversion in general nor with cracking, isomerization or hydrocracking specifically. It is, rather, concerned with converting $C_3^+$ olefins to higher molecular weight non-aromatic hydrocarbons and aromatic hydrocarbons which provide exceptional use as gasoline components. The instant invention, further, is not concerned with use of small or intermediate pore size zeolite catalysts, e.g. shape selective catalysts, but rather with use of large pore, i.e. greater than 6 Angstrom, zeolites. It is not concerned with use of catalysts comprising $SiO_2/Al_2O_3$ mole ratios normally used in olefin conversions or with acidic catalysts, but rather with use of high $SiO_2/Al_2O_3$ mole ratio zeolites in catalyst compositions having rather low acid activity.

SUMMARY OF THE INVENTION

In accordance with the present invention, there is provided a process for converting feedstock comprising $C_3^+$ olefins, preferably olefins of from three carbon atoms to about six carbon atoms, in the absence of added hydrogen, to product comprising non-aromatic hydrocarbons of higher molecular weight than the feedstock olefins and aromatic hydrocarbons, said process comprising contacting said feedstock at conversion conditions with a catalyst comprising a crystalline zeolite having large pores, i.e., essentially all pores of critical diameter greater then about 6 Angstrom Units, and a high silica/alumina mole ratio, i.e. greater than about 50.

It is important to note that the present process provides a highly useful gasoline-boiling range product with substantially reduced polynuclear aromatic compounds and reduced coke when compared to other olefin conversion processes. Also, the present process provides improved aromatics selectively when compared to such other processes utilizing different catalysts. It is further noted that the catalyst for use herein does not require a hydrogenation/dehydrogenation component.

BRIEF DESCRIPTION OF THE DRAWING

The FIGURE is a plot of aromatic selectivity data relative conversion generated by specific examples hereinafter set forth for comparison of the present process with other olefin conversion processes.

SPECIFIC EMBODIMENTS

The feedstock to the present process will comprise olefins of three or more carbon atoms, preferably from three to about six carbon atoms, such as, for example, propylene, butenes, pentenes, hexenes, and mixtures thereof. Olefins which may be included in feedstock to the present process may be derived from various refinery or chemical plant product and by-product sources including decomposition, dehydrogenation, polymerization, depolymerization and dealkylation. Thermal and catalytic decomposition, or cracking, is an important source of such olefins in the refinery where paraffins and naphthenic hydrocarbons are converted to unsaturated hydrocarbons.

The type reactor for use in the instant invention is not critical, but a fluidized or moving bed reactor is preferred, especially with an operation mode allowing periodic catalyst regeneration such as by, for example, pyrolysis of the catalyst in air to remove coke and other contaminants normally deposited on the catalyst by such process operation.

The zeolites used in the present catalysts have a porous crystalline structure with essentially all pores having at least one dimension in excess of 6 Angstroms. Therefore, the pores and channels of the zeolite useful herein will be composed exclusively of 12-membered rings. The zeolite is also to have a silica/alumina ratio of at least 50 and a hydrocarbon sorption capacity for n-hexane of at least 6 percent. The hydrocarbon sorption capacity is determined by measuring the sorption at 25° C., 20 mm Hg (2666 Pa) hydrocarbon pressure in an inert carrier such as helium.

Hydrocarbon sorption capacity (%) =

$$\frac{\text{Wt. of hydrocarbon sorbed}}{\text{Wt. of zeolite}} \times 100$$

The sorption test is conveniently carried out in a thermogravimetric analyzer with helium as a carrier gas flowing over the zeolite at 25° C. The hydrocarbon of interest in this test procedure, e.g. n-hexane, is introduced into the gas stream adjusted to 20 mm Hg hydrocarbon pressure and the hydrocarbon uptake, measured as the increase in zeolite weight, is recorded. The sorption capacity may then be calculated as a percentage.

Consistent with the prescribed values of pore size and hydrocarbon sorption the zeolite should also have a Constraint Index of less than about 2.0, usually about 0.5 to less than about 2.0. Constraint Index provides a convenient measure of the extent to which a zeolite provides controlled access, for molecules of varying sizes to its internal structure. Zeolites which provide highly restricted access to and egress from the internal structure have a high value for the Constraint Index and zeolites of this kind usually have pores of small size. Zeolites which provide relatively free access to the internal zeolite structure have a low value for the Constraint Index. The method by which Constraint Index is determined is described fully in U.S. Pat. No. 4,016,218, incorporated herein by reference for details of the method together with examples of Constraint Index for some typical zeolites. Because Constraint Index is related to the crystalline structure of the zeolite but is nevertheless determined by means of a test which exploits the capacity of the zeolite to engage in a cracking reaction, that is, a reaction dependent upon the possession of acidic sites and functionality in the zeolite, the sample of zeolite used in the test should be representative of zeolitic structure whose Constraint Index is to be determined and should also possess requisite acidic functionality for the test. Acidic functionality may, of course, be varied by means including base exchange, steaming or control of silica/alumina ratio.

Zeolites of the requisite pore size, hydrocarbon sorption capacity and Constraint Index include high silica/alumina synthetic faujasite-type materials, especially those having the structure of zeolite Y, and zeolites ZSM-20 and Beta.

The large pore crystalline zeolite useful as a catalyst component herein will also have a high silica/alumina mole ratio of greater than about 50, preferably greater than about 100 and even more preferably greater than about 200.

No hydrogenation/dehydrogenation component is required, or, in fact, desired for the catalyst to be used in the present invention.

Of the above-listed examples of large pore crystalline zeolites for use as a catalyst component herein, zeolite Beta is described in U.S. Pat. No. 3,308,069 and Re. No. 28,341, the entire contents of each being incorporated herein by reference. The preferred form of zeolite Beta for use herein will, of course, have a silica/alumina mole ratio greater than 50. Preparing said zeolite Beta with a silica/AlO$_2$ mole ratio above the 100 maximum specified in U.S. Pat. No. 3,308,069 and Re. No. 28,341 would provide a more preferred zeolite component. One such zeolite preparation method comprises dealumination by extraction with acid.

Other large pore zeolites listed above for use as catalyst component in the present invention are those having the structure of zeolite Y and zeolite ZSM-20. Zeolite Y can be synthesized only in forms which have silica/alumina ratios up to about 5 and in order to achieve higher ratios, resort may be made to various techniques to remove structural aluminum so as to obtain a more highly siliceous zeolite. Zeolite ZSM-20 may be directly synthesized with silica/alumina ratios of 7 or higher, typically in the range of 7 to 10, as described in U.S. Pat. Nos. 3,972,983 and 4,021,331, the entire contents of each being incorporated herein by reference.

Control of the silica/alumina ratio of the zeolite in its as-synthesized form may be exercised by an appropriate selection of the relative proportions of the starting materials, especially the silica and alumina precursors, a relatively smaller quantity of the alumina precursor resulting in a higher silica/alumina ratio in the product zeolite, up to the limit of the synthesis procedure. If higher ratios are desired and alternative synthesis affording the desired high silica/alumina ratios are not available, other techniques such as those described below may be used in order to prepare the desired highly siliceous zeolites.

It should be understood that the silica/alumina mole ratios referred to in this specification are the structural or framework ratios, that is, the ratio for the SiO$_4$ to the AlO$_4$ tetrahedra which together constitute the structure of which the zeolite is composed. This ratio may vary from the silica/alumina ratio determined by various physical and chemical methods. For example, a gross chemical analysis may include alumina which is present in the form of cations associated with the acidic sites on the zeolite, thereby giving a low silica/alumina ratio. Similarly, if the ratio is determined by thermogravimetric analysis of ammonia desorption, a low ammonia titration may be obtained if cationic aluminum prevents exchange of the ammonium ions onto the acidic sites. These disparities are particularly troublesome when certain treatments such as the dealuminization methods described below which result in the presence of ionic aluminum free of the zeolite structure are employed. Due care should therefore be taken to ensure that the framework silica/alumina mole ratio is correctly determined.

A number of different methods are known for increasing the structural silica/alumina mole ratio of various zeolites. Many of these methods rely upon the removal of aluminum from the structural framework of the zeolite by chemical agents appropriate to this end. A considerable amount of work on the preparation of aluminum deficient faujasites has been performed and is reviewed in Advances in Chemistry Series No. 121, Molecular Sieves, G. T. Kerr, American Chemical Society, 1973. Specific methods for preparing dealuminized zeolites are described in the following, which are incorporated by reference herein for details of the methods: Catalysis by Zeolites (International Symposium on Zeolites, Lyon, Sept. 9-11, 1980), Elsevier Scientific Publishing Co., Amsterdam, 1980 (dealuminization of zeolite Y with silicon tetrachloride); U.S. Pat. No.

3,442,795 and G.B. Pat. No. 1,058,188 (hydrolysis and removal of aluminum by chelation); G.B. Pat. No. 1,061,847 (acid extraction of aluminum); U.S. Pat. Nos. 3,493,519 (aluminum removal by steaming and chelation); 3,591,488 (aluminum removal by steaming); 4,273,753 (dealuminization by silicon halides and oxyhalides); 3,691,099 (aluminum extraction with acid); 4,093,560 (dealuminization by treatment with salts); 3,937,791 (aluminum removal with Cr(III) solutions); 3,506,400 (steaming followed by chelation); 3,640,681 (extraction of aluminum with acetylacetonate followed by dehydroxylation); 3,836,561 (removal of aluminum with acid); Japan Pat. No. 53,101,003 (treatment with EDTA or other materials to remove aluminum) and J. Catalysis 54 295 (1978) (hydrothermal treatment followed by acid extraction).

Highly siliceous forms of zeolite having the structure of zeolite Y may be prepared by steaming or by acid extraction of structural aluminum (or both) but because zeolite Y in its normal, as-synthesized condition, is unstable to acid, it must first be converted to an acid-stable form. Methods for doing this are known and one of the most common forms of acid-resistant zeolite Y is known as "Ultrastable Y" (USY); it is described in U.S. Pat. Nos. 3,293,192 and 3,402,996 and the publication, Society of Chemical Engineering (London) Monograph Molecular Sieves, page 186 (1968) by C. V. McDaniel and P. K. Maher, and incorporation herein by reference is made to these for details of the zeolite and its preparation. In general, "ultrastable" refers to Y-type zeolite which is highly resistant to degradation of crystallinity by high temperature and steam treatment and is characterized by a $R_2O$ content (wherein R is Na, K or any other alkali metal ion) of less than 4 weight percent, preferably less than 1 weight percent, and a unit cell size less than 24.5 Angstroms and a silica/alumina mole ratio in the range of 3.5 to 7 or higher. The ultrastable form of Y-type zeolite is obtained primarily by a substantial reduction of the alkali metal ions and the unit cell size. The ultrastable zeolite is identified both by the smaller unit cell and the low alkali metal content in the crystal structure.

Other specific methods for increasing the silica/alumina mole ratio of zeolite Y by acid extraction are described in U.S. Pat. Nos. 4,218,307, 3,591,488 and 3,691,099, incorporated herein by reference for details of these methods.

Zeolite ZSM-20 may be converted to more highly siliceous forms by a process similar to that used for zeolite Y. First, the zeolite may be converted to an "ultrastable" form which is then dealuminized by acid extraction. The conversion to the ultrastable form may suitably be carried out by the same sequence of steps used for preparing ultrastable Y. The zeolite is successively base-exchanged to the ammonium form and calcined, normally at temperatures above 700° C. The calcination should be carried out in a deep bed in order to impede removal of gaseous products. Acid extraction of the "ultrastable" ZSM-20 may be effected in the same way as described above for zeolite Beta.

The large pore, high silica/alumina zeolite component may be incorporated with another material resistant to the temperature and other conditions employed in the process. Such matrix materials include synthetic or natural substances as well as inorganic materials such as clay, silica and/or metal oxides. The latter may be either naturally occurring or in the form of gelatinous precipitates or gels including mixtures of silica and metal oxides. Naturally occurring clays which can be composited with the catalyst include those of the montmorillonite and kaolin families. These clays can be used in the raw state as originally mined or initially subjected to calcination, acid treatment or chemical modification.

The catalyst may include other components of porous matrix material, such as alumina, silica-alumina, silica-magnesia, silica-zirconia, silica-thoria, silica-berylia, silica-titania, as well as ternary compositions, such as silica-alumina-thoria, silica-alumina-zirconia, silica-alumina-magnesia, and silica-magnesia zirconia. The matrix may be in the form of a cogel with the zeolite. The relative proportions of zeolite component and inorganic oxide gel matrix may vary widely with the zeolite content ranging from between 1 to 99, more usually 5 to 80, percent by weight of the composite.

The present process will be conducted in the absence of added hydrogen and at conversion conditions including a temperature of from about 200° C. to about 700° C., preferably from about 350° C. to about 510° C., a pressure of from about 0 psig to about 1000 psig, preferably for about atmospheric pressure to about 500 psig, and a weight hourly space velocity of from about 0.1 $hr^{-1}$ to about 200 $hr^{-1}$, preferably from about 0.5 $hr^{-1}$ to about 20 $hr^{-1}$.

The following examples will serve to illustrate the present invention.

EXAMPLE 1

Two catalysts (A and B) for use in the present process as well as several catalysts (C, D and E) not comparably suitable for the present process were prepared for process exemplification and generation of comparative data. Catalysts A and B were high silica/alumina, large pore, low acid activity materials for use in the present invention.

Catalyst A was composed of the hydrogen form of zeolite having the structure of zeolite Y produced by a deep bed calcination of a parent zeolite Y followed by washing with 2N HCl solution and calcination. More particularly, 100 grams of conventional Linde NaY were mixed with 167 grams NH$_4$Cl and 276 grams of demineralized water, and the slurry was heated to 82° C. for 2 hours. The slurry was then filtered hot and washed with 2 liters of demineralized water. This procedure was carried out twice more and was followed by calcination in a covered dish for three hours at 760° C. Subsequently, the resulting zeolite was exchanged with NH$_4$Cl three more times followed by another calcination at 815° C. for three hours. The resulting zeolite was washed with 2N HCl for 2½ hours at 70° C. The final silica/alumina mole ratio of Catalyst A was 226 and the Alpha Value thereof was about 5.

Catalyst B was composed of the hydrogen form of zeolite Beta produced by severe streaming (649° C. at 2 atmospheres pressure for 24 hours) of fresh hydrogen-Beta having a silica/alumina mole ratio of 30. The final Catalyst B had a silica/alumina mole ratio of 290 and an Alpha Value of 1.6. The structures of both the unsteamed and steamed zeolite were confirmed to be Beta by matching X-ray diffraction patterns with those provided in U.S. Pat. No. 3,308,069 and Re. No. 28,341. Both Catalysts A and B exhibit pores of greater than 6 Angstroms.

Catalyst C was the hydrogen form of zeolite ZSM-12 prepared according to U.S. Pat. No. 3,970,544, the entire contents of which is incorporated herein by reference. Catalyst C had a silica/alumina mole ratio of 118, but about half of its pores were of less than 6 Angstrom size. The structure of this zeolite was determined by X-ray analysis to be that of ZSM-12 (U.S. Pat. No. 3,832,499) having a dual system of channels, about one-half of which are composed of 10-membered rings allowing for a pore size of 5-6 Angstroms and about one-half of which are composed of 12-membered rings allowing for a pore size of 8-9 Angstroms. The Contraint Index for this zeolite is 2.0. Its Alpha Value was 100.

Catalyst D was composed of a large pore, i.e. greater than 6 Angstroms, zeolite having a silica/alumina mole ratio of only 5. Catalyst D was the commercial rare earth form of zeolite Y in an amorphous silica/alumina binder. The overall Alpha Value of Catalyst D, containing 8% zeolite, was 0.4. X-ray diffraction analysis confirmed the zeolite Y structure.

Catalyst E was the hydrogen form of zeolite ZSM-5 prepared according to U.S. Pat. No. 3,702,886, the entire contents of which is incorporated herein by reference. Catalyst E had a silica/alumina mole ratio of 70, an Alpha Value of 250 and a critical pore dimension of not greater than about 6 Angstroms. X-ray diffraction analysis confirmed the zeolite ZSM-5 structure.

Each of the catalysts was sized to 60-80 mesh. The following Table 1 lists critical catalyst properties of the above catalysts.

TABLE 1

| Catalyst | A | B | C | D | E |
|---|---|---|---|---|---|
| Pore Size, Angstroms | 8-9 | 8-9 | 5-6 and 8-9 | 8-9 | 5-6 |
| $SiO_2/Al_2O_3$, molar | 226 | 290 | 118 | 5 | 70 |
| Alpha Value | 5 | 1.6 | 100 | 0.4 | 250 |

As is known in the art, the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (rate constant=0.016). The Alpha Test is described in U.S. Pat. No. 3,354,078, incorporated herein by reference for that description, and in The Journal of Catalysis, Vol. IV, pp. 522-529 (August 1965).

EXAMPLE 2

In a series of experiments, members of the homologous series of $C_2$ to $C_5$ nomral olefins were passed separately through a fluidized bed of fresh Catalyst A at 410° C., atmospheric pressure and a liquid hourly space velocity of 4 $hr^{-1}$. Products of the experiments were analyzed and are presented in Table 2. Surprisingly small amounts of coke (i.e., less than 0.4%) and dry gas (i.e., $C_1+C_2$ of less than or equal to 0.4%) were produced in each experiment. Of particular note were the low concentrations of aromatics higher than $C_{12}$ produced, indicating advantageous selectivity towards gasoline boiling range materials. The catalyst bed in each experiment contained 35 cc of catalyst mixed with 15 cc of 80-120 mesh vycor chips.

TABLE 2

| | Olefin Feedstock | | | |
|---|---|---|---|---|
| | $C_5$ | $C_4$ | $C_3$ | $C_2$ |
| Conversion, wt. % | 38.11 | 27.64 | 10.82 | 0 |
| Coke, wt. % | 0.4 | 0.35 | 0.28 | — |
| Liquid Products, wt. % | | | | |
| $C_5$-$C_{10}$ Non-aromatics | 73.4 | 73.3 | 68.2 | 0 |
| Benzene | 6.0 | 3.7 | 5.6 | 0 |
| Toluene | 1.0 | 0.4 | 2.4 | 0 |
| $C_8$ Aromatics | 5.4 | 9.5 | 9.3 | 0 |
| $C_9$ Aromatics | 7.2 | 5.8 | 6.9 | 0 |
| $C_{10}$ Aromatics | 7.0 | 5.2 | 5.9 | 0 |
| $C_{11}$ Aromatics | 0 | 1.6 | 1.0 | 0 |
| $C_{12}$ Aromatics | 0 | 0.3 | 0 | 0 |
| $C_{13}^+$ Aromatics | 0 | 0.2 | 1.6 | 0 |

EXAMPLES 3-19

In order to compare olefin conversion by way of the present process with other olefin conversion processes utilizing different catalysts, experiments were conducted using Catalysts A, B, C, D and E. The feedstock in each experiment was propylene.

In each experiment, the catalyst bed contained 35 cc of catalyst mixed with 15 cc of 80-120 mesh vycor chips. The experiment conditions and results are presented in Tables 3A, 3B and 3C below. The FIGURE provides graphic illustration of the beneficial aromatic selectivity provided by experiments identified as Examples 3, 5, 9 and 12-16, conducted in accordance with the present process over large pore, high silica/alumina catalysts when compared to the other olefin conversion processes.

TABLE 3A

| | Example Number | | | | | | |
|---|---|---|---|---|---|---|---|
| | 3 | 4 | 5 | 6 | 7 | 8 | 9 |
| Catalyst | A | D | B | C | E | E | A |
| Temperature, °C. | 410 | 410 | 410 | 410 | 410 | 410 | 510 |
| WHSV, $hr^{-1}$ | 2.2 | 2.0 | 2.0 | 2.0 | 2.0 | 153 | 0.6 |
| Conversion, wt. % | 20.88 | 82.66 | 39.31 | 81.29 | 98.53 | 41.88 | 50.45 |
| Selectivities* | | | | | | | |
| $C_1 + C_2$ | 0.97 | 2.32 | 0.79 | 1.95 | 2.38 | 0.51 | 3.00 |
| $C_3 + C_4$ | 50.78 | 34.08 | 30.96 | 33.95 | 55.61 | 27.42 | 39.91 |
| $C_5$-$C_{10}$ Non aromatics | 24.91 | 27.30 | 50.72 | 36.44 | 8.99 | 63.17 | 25.06 |
| Benzene | 4.84 | 6.12 | 4.96 | 8.03 | 2.94 | 6.01 | 4.25 |
| Toluene | 5.09 | 0.33 | 2.35 | 6.11 | 6.27 | 1.61 | 5.59 |
| $C_8$ Aromatics | 5.30 | 5.20 | 3.32 | 4.61 | 9.02 | 1.28 | 7.71 |
| $C_9$ Aromatics | 2.69 | 2.58 | 2.94 | 2.45 | 5.55 | 0 | 7.17 |
| $C_{10}$ Aromatics | 2.48 | 0.92 | 1.64 | 2.19 | 2.24 | 0 | 1.63 |
| $C_{11}$ Aromatics | 0 | 0 | 0.48 | 0.24 | 1.04 | 0 | 0.52 |
| $C_{12}$ Aromatics | 0 | 0 | 0.30 | 1.40 | 0.60 | 0 | 0 |
| $C_{13}^+$ Aromatics | 0.68 | 0.48 | 0.86 | 0 | 2.60 | 0 | 1.21 |
| Total Aromatics | 22.08 | 15.64 | 16.85 | 25.20 | 30.25 | 8.90 | 28.04 |
| Total Olefins | 38.26 | 19.68 | 54.02 | 42.12 | 8.79 | 76.46 | 16.97 |
| Total Paraffins | 37.40 | 46.02 | 28.45 | 30.22 | 58.17 | 14.64 | 51.00 |

TABLE 3A-continued

| | Example Number | | | | | | |
|---|---|---|---|---|---|---|---|
| | 3 | 4 | 5 | 6 | 7 | 8 | 9 |
| Coke, wt. % | 2.26 | 18.66 | 0.68 | 2.46 | 2.77 | 0 | 3.99 |

*Selectivity = amount obtained, wt. %/conversion, wt. %

TABLE 3B

| | Example Number | | | | | | |
|---|---|---|---|---|---|---|---|
| | 10 | 11 | 12 | 13 | 14 | 15 | 16 |
| Catalyst | E | E | A | A | A | B | B |
| Temperature, °C. | 410 | 410 | 510 | 510 | 350 | 410 | 410 |
| WHSV, hr$^{-1}$ | 185 | 70 | 2.0 | 4.6 | 0.6 | 0.8 | 1.3 |
| Conversion, wt. % | 27.65 | 80.52 | 28.24 | 22.29 | 10.93 | 72.00 | 57.02 |
| Selectivities* | | | | | | | |
| $C_1 + C_2$ | 1.28 | 1.39 | 4.61 | 5.01 | 0.43 | 2.11 | 1.13 |
| $C_3 + C_4$ | 26.30 | 32.88 | 50.90 | 50.95 | 35.83 | 53.09 | 39.88 |
| $C_5-C_{10}$ Non-aromatics | 64.27 | 43.40 | 20.96 | 19.00 | 41.88 | 15.74 | 39.04 |
| Benzene | 3.35 | 6.79 | 3.83 | 2.10 | 6.42 | 5.23 | 6.72 |
| Toluene | 1.84 | 8.51 | 4.15 | 3.37 | 4.93 | 2.88 | 4.57 |
| $C_8$ Aromatics | 2.96 | 1.69 | 6.79 | 8.03 | 5.34 | 7.54 | 3.96 |
| $C_9$ Aromatics | 0 | 3.30 | 3.78 | 5.15 | 3.04 | 7.67 | 2.31 |
| $C_{10}$ Aromatics | 0 | 1.32 | 1.87 | 1.90 | 1.54 | 3.58 | 1.85 |
| $C_{11}$ Aromatics | 0 | 0.44 | 0 | 0.88 | 0.23 | 1.29 | 0.29 |
| $C_{12}$ Aromatics | 0 | 0.27 | 0 | 0.03 | 0 | 0.43 | 0 |
| $C_{13}{}^+$ Aromatics | 0 | 0 | 1.36 | 1.27 | 0.44 | 0.07 | 0 |
| Total Aromatics | 8.15 | 22.34 | 21.67 | 22.74 | 21.86 | 28.69 | 19.70 |
| Total Olefins | 80.15 | 45.82 | 33.56 | 30.56 | 38.51 | 34.32 | 52.91 |
| Total Paraffins | 11.70 | 31.84 | 44.60 | 44.60 | 45.11 | 36.62 | 26.06 |
| Coke, wt. % | 0 | 0 | 1.86 | 2.30 | 0 | 0.40 | 0.25 |

*Selectivity = amount obtained, wt. %/conversion, wt. %

TABLE 3C

| | Example Number | | |
|---|---|---|---|
| | 17 | 18 | 19 |
| Catalyst | C | C | C |
| Temperature °C. | 410 | 410 | 410 |
| WHSV, hr$^{-1}$ | 30 | 15 | 5.8 |
| Conversion, wt. % | 11.4 | 35.52 | 55.94 |
| Selectivities* | | | |
| $C_1 + C_2$ | 0.26 | 0.48 | 0.45 |
| $C_3 + C_4$ | 0.30 | 30.44 | 41.80 |
| $C_5-C_{10}$ Non-aromatics | 64.95 | 63.70 | 45.80 |
| Benzene | 0.01 | 1.49 | 1.84 |
| Toluene | 3.98 | 3.71 | 5.98 |
| $C_8$ Aromatics | 0 | 0 | 1.55 |
| $C_9$ Aromatics | 0 | 0 | 1.76 |
| $C_{10}$ Aromatics | 0 | 0 | 0.30 |
| $C_{11}$ Aromatics | 0 | 0 | 0 |
| $C_{12}$ Aromatics | 0 | 0 | 0 |
| $C_{13}{}^+$ Aromatics | 0 | 0 | 0.28 |
| Total Aromatics | 3.99 | 5.20 | 11.71 |
| Total Olefins | 78.10 | 78.92 | 73.80 |
| Total Paraffins | 17.67 | 15.70 | 14.25 |
| Coke, wt. % | 0.24 | 0.20 | 0.20 |

*Selectivity = amount obtained, wt. %/conversion, wt. %

What is claimed is:

1. A process for converting feedstock comprising $C_3{}^+$ olefins to product comprising non-aromatic hydrocarbons of higher molecular weight than feedstock olefins and aromatic hydrocarbons comprising contacting said feedstock in the absence of added hydrogen at conversion conditions with a catalyst comprising a crystalline zeolite having a Constraint Index of less than about 2 and a silica/alumina mole ratio greater than about 100.

2. The process of claim 1 wherein said feedstock comprises olefins of from 3 to about 6 carbon atoms.

3. The process of claim 2 wherein said olefins are selected from the group consisting of propylene, butenes, pentenes, hexenes and mixtures thereof.

4. The process of claim 1 wherein said silica/alumina mole ratio is greater than about 200.

5. The process of claim 1 wherein said zeolite posesses a hydrocarbon sorption capacity for n-hexane of at least 6 percent.

6. The process of claim 1, 2, 3, 4 or 5 wherein said zeolite has a Contraint Index of from about 0.5 to less than about 2.

7. The process of claim 1 wherein said conversion conditions include a temperature of from about 200° C. to about 700° C., a pressure of from about 0 psig to about 1000 psig and a weight hourly space velocity of from about 0.1 hr$^{-1}$ to about 200 hr$^{-1}$.

8. The process of claim 7 wherein said conversion conditions include a temperature of from about 350° C. to about 510° C., a pressure of from about atmospheric to about 500 psig and a weight hourly space velocity of from about 0.5 hr$^{-1}$ to about 20 hr$^{-1}$.

9. A process for converting feedstock comprising $C_3{}^+$ olefins to product comprising non-aromatic hydrocarbons of higher molecular weight than feedstock olefins and aromatic hydrocarbons comprising contacting said feedstock in the absence of added hydrogen at conversion conditions with a catalyst comprising a crystalline zeolite having a Constraint Index of less than about 2, a silica/alumina mole ratio greater than about 200 and the structure of zeolite Beta.

10. A process for converting feedstock comprising $C_3{}^+$ olefins to product comprising non-aromatic hydrocarbons of higher molecular weight than feedstock olefins and aromatic hydrocarbons comprising contacting said feedstock in the absence of added hydrogen at conversion conditions with a catalyst comprising a crystalline zeolite having a Constraint Index of less than about 2, a silica/alumina mole ratio greater than about 50 and the structure of zeolite Y.

* * * * *